United States Patent [19]

Cocherell et al.

[11] Patent Number: 4,812,306
[45] Date of Patent: Mar. 14, 1989

[54] TOOTHPASTE OR DENTAL CREAM COMPOSITION AND METHOD OF PREPARING SAME

[76] Inventors: Francis E. Cocherell, 809 Silver Maple Dr., Azusa; Homer C. Harper, 15102 E. Chetney, Baldwin Park, both of Calif. 91702; George Hsieh, 23943 Sunset Crossing Rd., Diamond Bar, Calif. 91765

[21] Appl. No.: 139,064

[22] Filed: Dec. 21, 1987

Related U.S. Application Data

[63] Continuation of Ser. No. 819,583, Jan. 17, 1986, abandoned.

[51] Int. Cl.$^4$ .......................... A61K 7/26; A61K 7/18
[52] U.S. Cl. ......................................... 424/52; 424/49; 424/58; 424/56
[58] Field of Search ...................... 424/49, 52, 58, 56

[56] References Cited

U.S. PATENT DOCUMENTS

| | | | |
|---|---|---|---|
| 3,518,344 | 6/1970 | Welsh | 424/44 |
| 3,577,492 | 5/1971 | Welsh | 264/120 |
| 3,937,804 | 2/1976 | Delaney | 424/52 |
| 4,098,878 | 7/1978 | Baines | 424/52 |
| 4,132,771 | 1/1979 | Schreiber | 424/52 |
| 4,159,315 | 6/1979 | Wagenknecht | 424/48 |
| 4,160,022 | 7/1979 | Delaney | 424/52 |
| 4,522,805 | 6/1985 | Gordon | 424/52 |
| 4,525,342 | 6/1985 | Weiss | 424/49 |
| 4,528,180 | 7/1985 | Schaeffer | 424/52 |

*Primary Examiner*—Ronald W. Griffin
*Assistant Examiner*—F. T. Moezie

[57] ABSTRACT

A water-free dental cream or toothpaste composition comprising 6% to 90% by total weight of one or more hydrogenated vegetable oils, 0.02% to 25% by total weight of one or more flavoring oils or extracts, 0.1% to 60% by total weight of glycerin, 0.2% to 25% by total weight of cornstarch, 10% to 90% by total weight of one or more inorganic salts selected from the group comprising sodium bicarbonate, magnesium sulfate and sodium chloride, 0.001% to 3.5% by total weight of one or more flourides selected from the group comprising sodium flouride, potassium flouride and ammonium flouride, 0.01% to 5% by total weight of sacchrin or aspartame, and 0.01% to 5% by total weight of sodium lauryl sulfate.

8 Claims, No Drawings

TOOTHPASTE OR DENTAL CREAM COMPOSITION AND METHOD OF PREPARING SAME

This application is a continuation of application Ser. No. 819,583, filed 1/17/86, now abandoned.

FIELD OF THE INVENTION

The present invention generally relates to a dentrifice composition and more particularly to a water-free dental cream or toothpaste wherein a non-humectant, anhydrous binder is present as a carrier for a chemotherapeutic inorganic salt, particularly sodium bicarbonate. The carrier is comprised of one or more hydrogenated vegetable oils.

BACKGROUND OF THE INVENTION

Teeth are very unique in the human body in that they are the only body tissue that are not subject to metabolic turnover. Once our permanent teeth are formed, theoretically they are almost indestructible. For this reason, it is easy to understand the important role of teeth in archeological diggings since they are preserved in the fossil records. Another area in which teeth play an important role is in the area of forensic dentistry.

In spite of their seemingly indestructible nature, teeth are constantly subjected to bacterial attack throughout a person's lifetime. Such bacterial attach manifests itself in the form of various periodontal diseases including dental caries. Periodontal disease ranks as the ost universal affliction suffered by mankind. As of 1977, it was estimated that, in the United States alone, the cost of treating various periodontal diseases exceeded 11 billion dollars.

Bacterial plaque has been shown to be a leading cause of disease of the teeth and of the periodontium. Plaque results from the interaction of mucin, a conjugated protein present in human saliva with various micro-organisms present throughout the oral flora. Bacterial plaque causes decalcification of the enamel layer of the tooth structure. The disintegration of enamel is accomplished by both enzymes as well as acids formed from the bacterial colonies within the plaque.

Several specific species of micro-organism have been implicated in the human periodontal disease during recent studies. These micro-organisms which are present in subgingival plaque are believed to play an important role as agents in causing this destructive disease. A small group of mostly gram positive anaerobic bacteria, from more than 200 morphologically and biochemically distinct species which have been isolated from human periodontal pockets, has been closely related with diseased sites exhibiting inflamation, destruction of the periodontal attachment and crestal alveolar bone. Included within this group are strains of oral spirochetes, *Bacteroides gingivalis, Bacteroides intermedius. Fusobacterium numcleatum, Ekenella corrodens,* Eubacterium sp, *Actinobacillus actinomycetemcomitans, Selennomnonas sputigena,* and *Wolinella recta.*

The above micro-organisms have been shown to be present in periodontal lesion and have been shown to possess potentially pathogenic virulence factors which account for their attachment and proliferation below the tissue. Furthermore, they inhibit host defense mechanisms while creating periodontal tissue damage.

Other recent studies have shown that sodium bicarbonate as well as other inorganic salts such as sodium chloride and magnesium sulfate have beneficial therapeutic properties when used as a chemotherapeutic agent for treatment of oral micro-organisms associated with periodontal disease. These inorganic salts were shown to be rapidly bacteriocidal to oral spirochetes and motile rods by inducing, after brief in vitro exposure, ultrastructural changes toxic to periodontal disease organisms. These anti-microbial agents were active against all suspected periodontopathogens tested. Sodium bicarbonate at a concentration of 84,000 ppm was found to produce in vitro a 99% lethality to selected strains of B intermedium and F nucleatum within 15 to 30 minutes after exposure.

The use of pure sodium bicarbonate has already been proven very effective in the removal of dental plaque and has also been shown to be effective in the control of periodontal disease. Sodium bicarbonate in powder form has been used for a number of years, however, it has never gained widespread acceptance by the public since it is inconvenient and difficult to use in powder form. At present, there is no sodium bicarbonate toothpaste on the market that is available for consumer use.

SUMMARY AND OBJECTS OF THE INVENTION

The present invention fulfills a long-felt but previously unsolved need by incorporating sodium bicarbonate as well as other inorganic salts into a water-free dental cream or toothpaste composition for use as a chemotherapeutic agent in the treatment of oral micro-organisms associated with periodontal disease. The invention further includes the use of one or more hydrogenated oils as a carrier or medium for the sodium bicarbonate or other inorganic salts. The use of hydrogenated oils is essential in that they do not chemically react with the sodium bicarbonate. Sodium bicarbonate, when in the presence of small amounts of water, will give off carbon dioxide gas forming sodium carbonate and carbonic acid. As sodium carbonate is much more alkaline than sodium bicarbonate, it adds a very bitter taste which is very difficult to mask in a toothpaste. All previous toothpaste preparations have been comprised of an aqueous mixture using a humectant with water present in varying quantities. The use of hydrogentated oils allows the present toothpaste preparation to be water-free, thereby preventing the formation of undesirable sodium carbonate.

The dental cream or toothpaste of the present invention is prepared by combining flavoring oils and glycerin to form a liquid mixture, thickening the liquid mixture by the addition of corn starch, kneading the thickened mixture to form a dough-like mass and subsequently drying the dough-like mass. After sufficient drying, the dough-like mass becomes dry and crumbly and is subsequently ground to form a powder. The powder is then mixed with one or more inorganic salts as well as with other dry ingredients including flouride, a sweetener such as aspartame or sacchrin, and sodium lauryl sulfate to form a powder mixture which is combined with one or more hydrogenated oils and whipped until a cream or paste of the desired consistency is obtained.

It is therefore an object of the present invention to provide a water-free dental cream or toothpaste composition including one or more chemotherapeutic inorganic salts.

Another object of the present invention is to provide a method of incorporating a liquid masking or flavoring agent into a dental cream or toothpaste composition without changing the viscosity of a hydrogenated binder of the product and without eventual separation of the flavoring oils.

A still further object of the present invention is to provide a water-free dental cream or toothpaste which is stable in nature with regard to the active ingredients.

Another object of the present invention is to provide a novel method of preparing a stable water-free dental cream or toothpaste.

These and other objects and advantages of the present invention will become apparent in view of the following detailed description.

DETAILED DESCRIPTION OF THE INVENTION

The water-free cream or toothpaste composition is comprised of between about 6% and 90% by total weight of one or more hydrogenated vegetable oils, between about 0.20% and 25% by total weight of one or more flavoring oils including oil extracts, between about 0.1% and 60% by total weight of glycerin, between about 0.2% and 25% by total weight of cornstarch, between about 10% and 90% by total weight of one or more inorganic salts, between about 0.001% and 3.5% by total weight of one or more flourides, between about 0.01% and 5% by total weight of sacchrin or aspartame, and between about 0.01% and 5% by total weight of sodium lauryl sulfate.

The hydrogenated vegetable oils include sunflower oil, soybean oils, coconut oil, as well as mono and diglycerides.

The flavoring oils or oil extracts may include anise oil, clove oil, sassafrass, peppermint, eugenol and Pemiento Gordo berry extract. Pemiento Gordo is a berry of the Myrtle tree or shrub family.

The inorganic salts may include sodium bicarbonate, magnesium sulfate and sodium chloride. In the case of sodium bicarbonate, optimum therapeutic results have been achieved when about 20% of the sodium bicarbonate particles are about 40 microns in diameter and the remaining 80% of particles vary in size down in diameter and the remaining 80% of particles vary in size down to about 1 micron or less in diameter. Such a particle size distribution maximizes cleaning efficiency without causing harmful tooth abrasion.

The fluorides may include sodium flouride, potassium flouride and ammonium flouride.

It is also possible to incorporate into the above toothpaste or dental cream composition between about 5% and 25% of a suitable silica abrasive.

EXAMPLE

Anise Oil U.S.P.: =1.481%
Clove Oil U.S.P.: =0.206%
Sassafrass U.S.P.: =0.823%
Peppermint U.S.P.: =1.646%
Glycerine U.S.P.: =11.695%
Cornstarch U.S.P.: =0.247%
Sodium Flouride: =0.247%
Sodium Sacchrin: =0.617%
Sodium Lauryl Sulfate: =0.617%
Sodium Bicarbonate: =35.076%
Hydrogenated Vegetable Oil 46.769%

The water-free dental cream or toothpaste composition is prepared by combining the flavoring oils or oil extracts with glycerin to form a liquid mixture, adding corn starch to the liquid mixture to form a thickened mixture, and kneading the thickened mixture to form a dough-like mass. The dough-like mass is placed into an air-tight container and allowed to dry for approximately eight hours. As drying occurs, the flavoring oils are absorbed by the corn starch and the dough-like mass turns lighter in color. After the drying period, absorption of the flavoring oils is complete and the dough-like mass turns into a dry, crumbly material which is not crystalline in nature. The now dried material is ground into a powder and combined with the remaining dry ingredients including the flourides, sacchrin or aspartame, sodium lauryl sulfate and the inorganic salts. This powder mixture is then whipped together with the hydrogenated oils until a cream or paste having the desired consistency is obtained.

By following the above procedure, a stable dental cream or toothpaste mixture is obtained. Since no water is present in the formulation, the inorganic salts including sodium bicarbonate do not undergo adverse chemical changes. Furthermore, the flavoring oils or oil extracts having been converted into powder form are prevented from separating out of the hydrogenated oils. The conversion of the flavoring oils into a powder form does not adversely affect their flavoring qualities.

A comparison was made of pure sodium bicarbonate, three leading commercially available toothpastes and the foregoing example of the present invention, based on the hypothesis that the longer after use that an alkaline pH remained in the mouth the longer the active ingredients were still effective. In the case of the three commercial toothpastes there was a relatively short period of rise in pH after brushing, to about 7 or 8. The pH then subsided to a baseline level of about 5, which was normal for the subject studied in this comparison, after a period of about 10–12 minutes. In the case of pure sodium bicarbonate a sharp rise in pH to a higher level (about 9) was detected, the subject's pH level then declining more gradually than in the case of the commercial toothpastes to about a normal pH of 5 at the expiration of 50 minutes after brushing.

In the case of the example of this invention, the subject's pH rose sharply to about 9 and the effects of the higher pH remained for a much longer period of time than in the case of the commercial pastes or pure sodium bicarbonate, the alkalinity gradually descending to a pH of 6.6 180 minutes after brushing. This was probably due a microscopic film or layer containing containing non-ionic sodium bicarbonate on the teeth and soft tissues which was slowly released into its ionic form thus creating a sustained relatively high pH level.

While this invention has been described in connection with different embodiments thereof, it will be understood that it is capable or further modifications, and this application is intended to cover any variations, uses, or adaptations of the invention following, in general, the principles of the invention and including such departures from the present disclosure as come within known or customary practice in the art to which the invention pertains, as may be applied to the essential features hereinbefore set forth and followed in the scope of the invention or the limits of the appended claims.

We claim:

1. A chemically stable anhydrous toothpaste or dental cream composition, comprising:
   (a) a powdery mixture of about 10% to about 90% by total weight of the composition of non-ionic sodium bicarbonate, about 0.02% to about 25% by total weight of the composition of a flavoring oil including flavoring oil extracts selected from the group consisting of anise oil, clove oil, sassafrass, peppermint, eugenol, Pemiento Gordo and mixtures thereof, about 0.001% to about 3.5% by total weight of the composition of a fluoride containing compound selected from the group consisting of sodium fluoride, potassium fluoride and ammonium fluoride, about 0.1% to about 60% by total weight of the composition of glycerin, about 0.01% to about 5% by total weight of the composition of a sweetener selected from the group consisting of saccharin and aspartame, about 0.01% to about 5% by total weight of the composition of sodium lauryl sulfate and about 0.2% to about 25% by total weight of the composition of corn starch, (b) said powdery mixture being uniformly present in about 6% to about 90% by total weight of the composition in an hydrogenated vegetable oil carrier selected from the group consisting of sunflower oil, soybean oil and coconut oil, said vegetable oil carrier and said powdery mixture having been whipped together to a desired cream or paste consistency.

2. A toothpaste or dental cream composition as in claim 1, wherein:

(a) said powdery mixture comprising about 12% by total weight of the composition of glycerin, about 35% by total weight of the composition of non-ionic sodium bicarbonate, about 4% by total weight of the composition of a mixture of flavoring oils consisting of anise oil, clove oil, sassafrass and peppermint, less than 1% by total weight of the composition of sodium fluoride, less than 1% by total weight of the composition of saccharin, less than 1% by total weight of the composition of sodium lauryl sulfate and less than 1% by total weight of the composition of cornstarch, and (b) about 47% by total weight of the composition of hydrogenated vegetable oil as said carrier.

3. A toothpaste or dental cream composition as in claim 1, wherein:

(a) about 20% of said non-ionic sodium bicarbonate having a particle size of about 40 microns in diameter and about 80% of said non-ionic sodium bicarbonate having a particle size ranging from about 1 micron to 40 microns in diameter.

4. A toothpaste or dental cream composition as in claim 1, wherein:

(a) said powdery mixture further including about 5% to about 25% by total weight of the composition of silica abrasive.

5. A chemically stable anhydrous toothpaste or dental cream composition, comprising:

(a) a powdery mixture suspended in an hydrogenated vegetable oil carrier selected from the group consisting of sunflower oil, soybean oil and coconut oil, said vegetable oil carrier and said powdery mixture having been whipped together to a desired cream or paste consistency; and, (b) said powdery mixture comprising non-ionic sodium bicarbonate, at least one flavoring oil or an extract thereof selected from the group consisting of anise oil, clove oil, sassafrass, peppermint, eugenol, Pemiento Gordo and mixtures thereof, a fluoride containing compound selected from the group consisting of sodium fluoride, potassium fluoride and ammonium fluoride, glycerin, a sweetener selected from the group consisting of saccharin and aspartame, sodium lauryl sulfate and corn starch, the powdery mixture ingredients having been mixed together, dried and then ground to a powdery consistency prior to having been mixed into said vegetable oil carrier.

6. The composition of claim 5, wherein said powdery mixture including from about 10% to about 90% by total weight of the total composition of non-ionic sodium bicarbonate, from about 0.02% to about 25% by total weight of the composition of the flavoring oil or extract thereof, from about 0.001% to about 3.5% by total weight of the composition of the fluoride containing compound, from about 0.1% to about 50% by total weight of the composition of said glycerin, from about 0.01% to about 5% by total weight of the composition of the sweetener, from about 0.01% to about 5% by total weight of the composition of said sodium lauryl sulfate and from about 0.2% to about 25% by total weight of the composition of said corn starch.

7. The composition of claim 5, wherein:

(a) the vegetable oil carrier comprising from about 6% to about 90% by total weight of the composition.

8. A toothpaste composition prepared by the steps of:

(a) combining one or more flavoring oils or flavoring oil extracts selected from the group consisting of anise oil, clove oil, sassafrass, peppermint, eugenol, and Peminento Gordo with glycerine and thereby forming a liquid mixture;

(b) adding a sufficient quantity of corn starch to the liquid mixture and thereby forming a thickened mixture;

(c) kneading the thickened mixture;

(d) drying the thickened mixture to a crumbly consistency;

(e) grinding the dried mixture into a powder and adding thereto a fluoride containing composition selected from the group consistig of sodium fluoride, potassium fluoride and ammonium fluoride and thereby forming a first dried component;

(f) adding to the first dried component a sweetener selected from the group consisting of saccharine and aspartame, and sodium lauryl sulphate and non-ionic sodium bicarbonate and thereby forming a powdery mixture; and, (g) adding the powdery mixture to an hydrogenated vegetable oil carrier selected from the group consisting of sunflower oil, soybean oil and coconut oil and whipping the resulting mixture to a desired cream or paste consistency.

* * * * *